(12) United States Patent
Robertson et al.

(10) Patent No.: US 10,086,199 B2
(45) Date of Patent: Oct. 2, 2018

(54) SYMPTOM-TREATMENT SYSTEM

(71) Applicant: James R. Robertson, Indianapolis, IN (US)

(72) Inventors: James R Robertson, Indianapolis, IN (US); Todd C Midkiff, Noblesville, IN (US); Andrew B Mendenhall, Mooresville, IN (US)

(73) Assignee: James R. Robertson, Indianapolis, IN (US)

( * ) Notice: Subject to any disclaimer, the term of this patent is extended or adjusted under 35 U.S.C. 154(b) by 0 days.

(21) Appl. No.: 14/177,948

(22) Filed: Feb. 11, 2014

(65) Prior Publication Data

US 2014/0303684 A1    Oct. 9, 2014

Related U.S. Application Data

(63) Continuation of application No. PCT/US2012/050536, filed on Aug. 13, 2012.

(60) Provisional application No. 61/522,550, filed on Aug. 11, 2011.

(51) Int. Cl.
| | |
|---|---|
| *A61N 1/36* | (2006.01) |
| *A61H 39/00* | (2006.01) |
| *A61N 1/04* | (2006.01) |
| *A61M 21/02* | (2006.01) |
| *A61N 1/05* | (2006.01) |
| *A61M 21/00* | (2006.01) |

(52) U.S. Cl.
CPC ....... *A61N 1/36021* (2013.01); *A61H 39/002* (2013.01); *A61M 21/02* (2013.01); *A61N 1/0476* (2013.01); *A61N 1/36014* (2013.01); *A61N 1/36032* (2013.01); *A61H 2201/165* (2013.01); *A61H 2205/021* (2013.01); *A61H 2205/027* (2013.01); *A61H 2205/04* (2013.01); *A61M 2021/0072* (2013.01); *A61M 2205/8206* (2013.01); *A61M 2209/088* (2013.01); *A61M 2210/0662* (2013.01); *A61N 1/0526* (2013.01)

(58) Field of Classification Search
CPC ................. A61N 1/36021; A61N 1/36032
USPC ........................................... 607/46
See application file for complete search history.

(56) References Cited

U.S. PATENT DOCUMENTS

| | | | | |
|---|---|---|---|---|
| 4,966,164 | A | * | 10/1990 | Colsen ............... A61H 39/002 128/907 |
| 5,058,605 | A | | 10/1991 | Slovak |
| 5,449,378 | A | | 9/1995 | Shouenborg |
| 5,514,175 | A | * | 5/1996 | Kim .................. A61H 39/002 607/115 |

(Continued)

FOREIGN PATENT DOCUMENTS

| | | |
|---|---|---|
| DE | 102006023824 A1 | 11/2007 |
| JP | 2005-006919 | 1/2005 |

(Continued)

OTHER PUBLICATIONS

International Search Report and Written Opinion, PCT/US2012/050536 dated Jan. 31, 2013.

*Primary Examiner* — Alyssa M Alter
(74) *Attorney, Agent, or Firm* — EIP US LLP (57) ABSTRACT

A symptom-treatment system includes a control unit configured to provide a treatment signal and a treatment unit coupled to the control unit to receive the treatment signal. The treatment unit is coupled to a patient to communicate the treatment unit to the patient.

7 Claims, 13 Drawing Sheets

(56) References Cited

U.S. PATENT DOCUMENTS

| | | | |
|---|---|---|---|
| 5,578,065 A | | 11/1996 | Hattori et al. |
| 5,824,022 A | * | 10/1998 | Zilberman ......... A61N 1/36032 128/903 |
| 6,091,989 A | | 7/2000 | Swerdlow et al. |
| 6,445,955 B1 | | 9/2002 | Michelson et al. |
| 7,336,993 B1 | | 2/2008 | Szeles |
| 7,660,637 B2 | | 2/2010 | Szeles |
| 7,781,486 B2 | | 8/2010 | Szeles |
| 2010/0168822 A1 | | 7/2010 | Szeles |
| 2011/0093049 A1 | | 4/2011 | Hinrichsen et al. |
| 2012/0226333 A1 | | 9/2012 | Szeles |

FOREIGN PATENT DOCUMENTS

| | | |
|---|---|---|
| JP | 2009537266 A | 10/2009 |
| WO | 2009154458 A2 | 12/2009 |
| WO | 2011030210 A1 | 3/2011 |

* cited by examiner

SYMPTOM-TREATMENT SYSTEM

BACKGROUND

The present disclosure relates to a therapeutic device, and in particular, to a therapeutic device for use on humans. More particularly, the present disclosure relates to a system for treating symptoms of pain, depression, anxiety, and sleeplessness.

SUMMARY

A symptom-treatment system includes a control unit configured to provide a treatment signal and a treatment unit coupled to the control unit and configured to transmit the treatment signal to a patient. The control unit is coupled to a patient to move there with.

In illustrative embodiments, the symptom-treatment system further comprises a control-unit mount. The control-unit mount is coupled to the control unit and configured to provide means for coupling selectively the control unit to the patient's ear at a location on patient's ear where the treatment unit is coupled to both the control unit and to the patient so that treatment signal is communicated from the control unit through the treatment unit and to the patient.

In illustrative embodiments, the control unit includes a control-unit housing formed to include a component space therein, a power source arranged to lie in the component space, and a control board arranged to lie in the control space and coupled to the power source to provide a treatment signal. The control-unit housing includes a grounding plate coupled to the control board and arranged to contact the patient's skin to cause an electrical circuit formed by the power source, the control board, and the grounding plate, the patient to be completed.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which:

FIGS. 4-15 are a series of views showing an assembly method for assembling the symptom-treatment system of FIGS. 1-3;

FIGS. 16-21 are a series of views showing a method of coupling the symptom-treatment system to the patient's ear;

DETAILED DESCRIPTION

Figure 1:
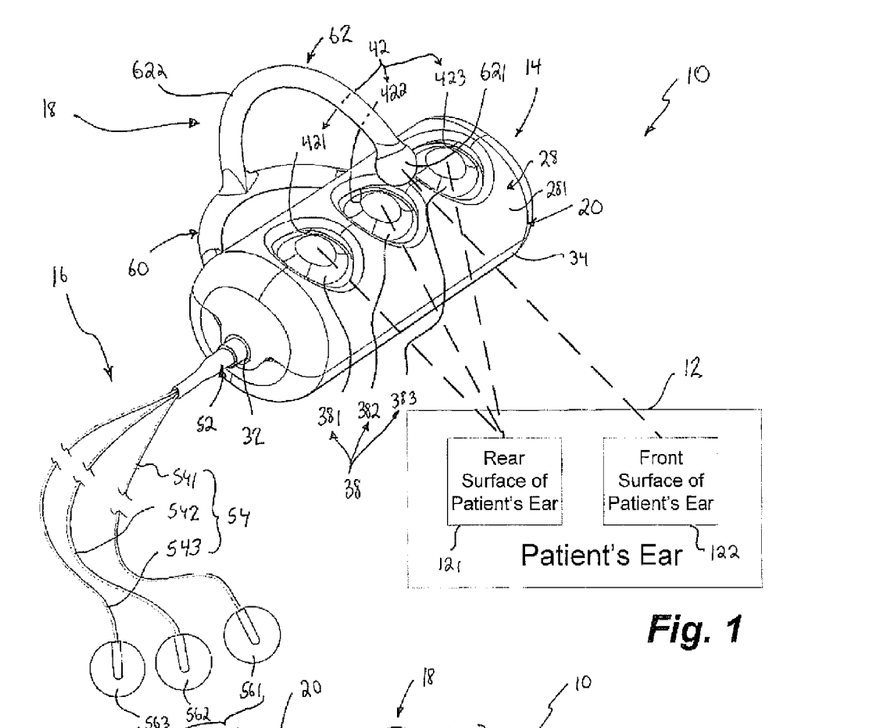
FIG. 1 is a perspective and diagrammatic view of a first embodiment of a symptom-treatment system in accordance with the present disclosure showing that the symptom-treatment system includes a cylindrical control unit having a set of three grounding terminals arranged to contact a rear surface of a patient's ear, a treatment unit including a set of treatment applicators configured to mount to a front surface of the patient's ear, and a C-shaped mount arranged to engage a front surface of the patient's ear to cause the control unit to be mounted on the patient's ear so that electrical stimulation provided by the control unit may be communicated to the treatment applicators so that therapy is provided to the patient.
Figure 2:
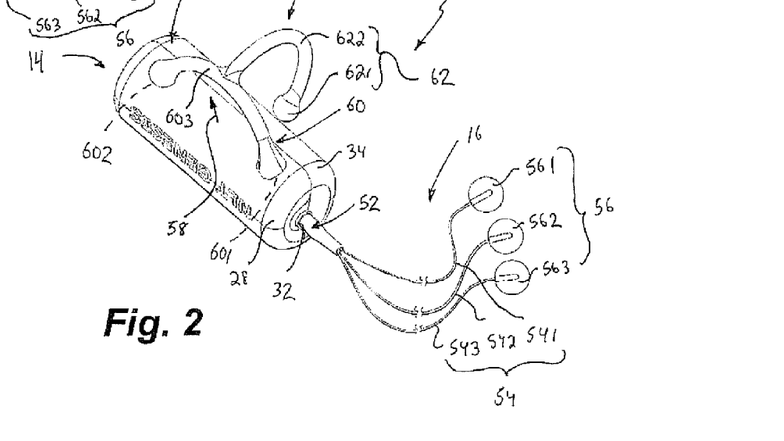
FIG. 2 is a rear-perspective view of the symptom-treatment system of FIG. 1 showing the C-shaped mount coupled to control unit.
Figure 3:
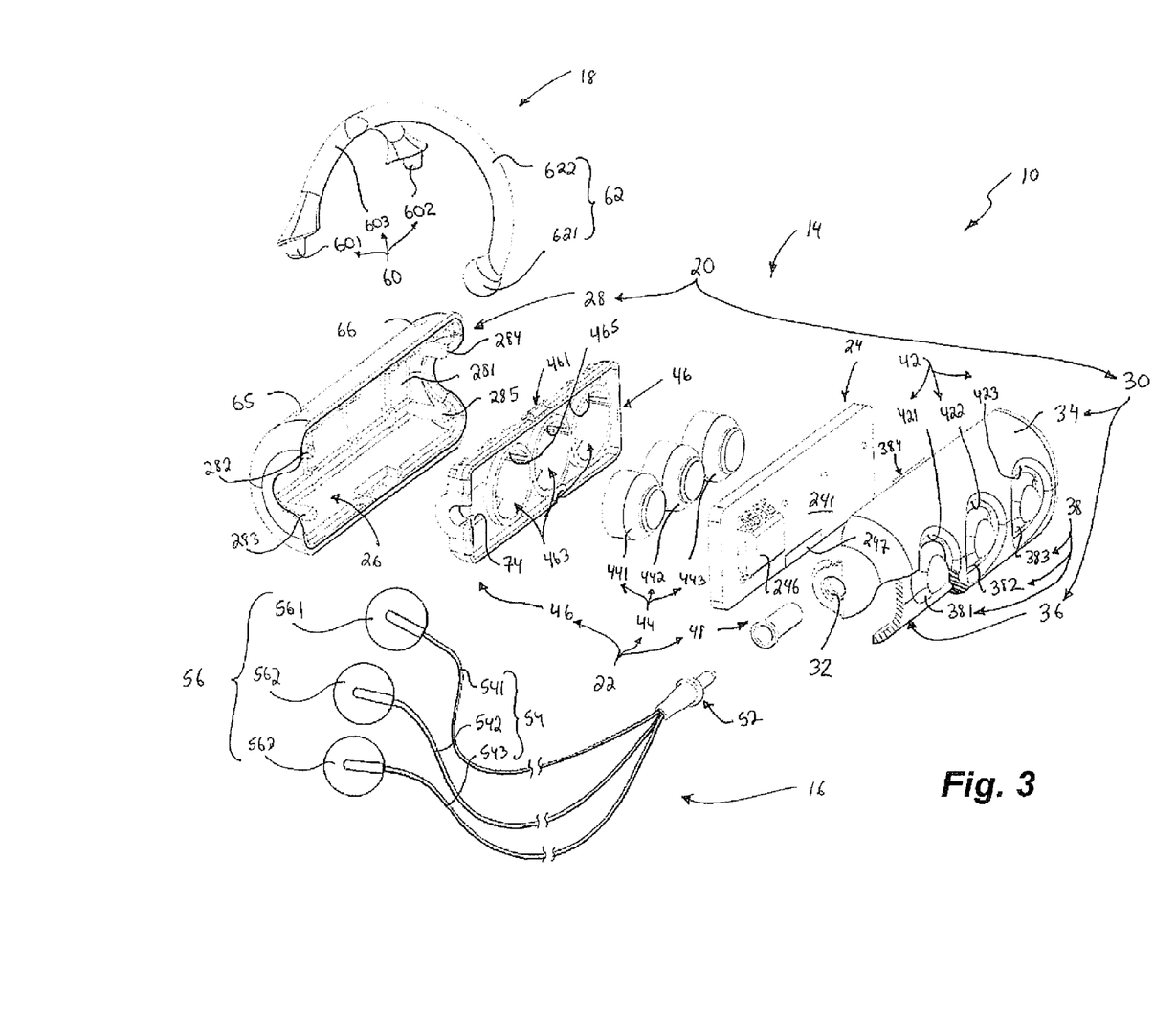
FIG. 3 is an exploded assembly view of the symptom-treatment system of FIGS. 1 and 2 showing that the symptom-treatment system includes, from top left to bottom right, a C-shaped mount, an upper mount shell, a power-source carrier, a set of three batteries, a control board, a control-unit foundation including a grounding plate having the set of three grounding terminals and a foundation shell over molded around the grounding plate, a plug receiver, and a treatment unit including a wire-harness plug, three connection wires, and three treatment applicators.
Figure 22:
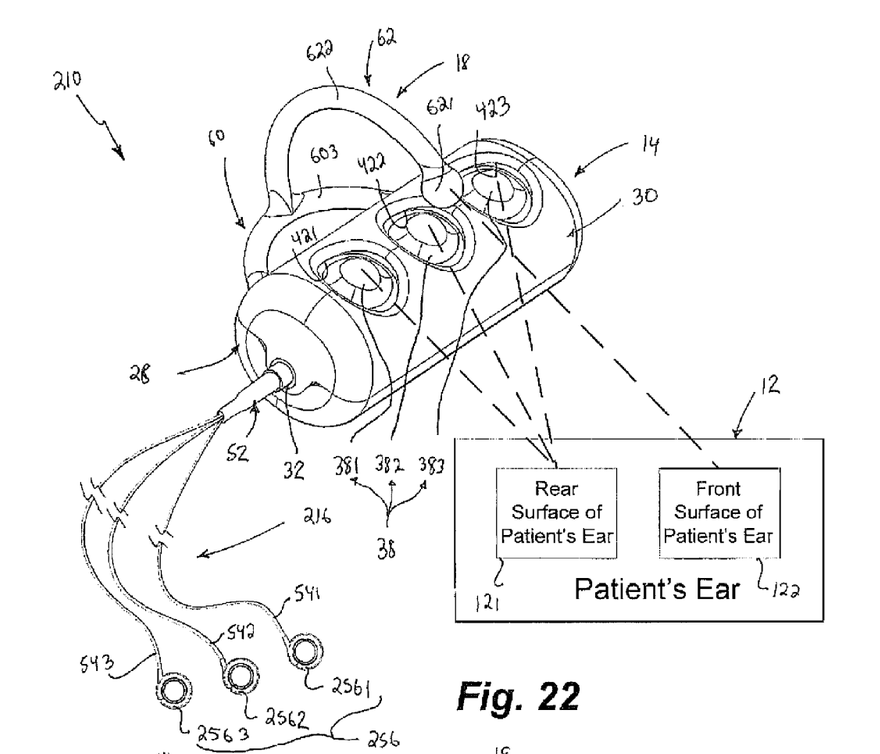
FIG. 22 is a perspective view and diagrammatic view of a another embodiment of a symptom-treatment system in accordance with the present disclosure showing that the symptom-treatment system includes the cylindrical control unit, a treatment unit including a set of treatment applicators that are configured to mate with an associated set of needles previously implanted on the front service of the patient's ear, and the C-shaped mount.
Figure 23:
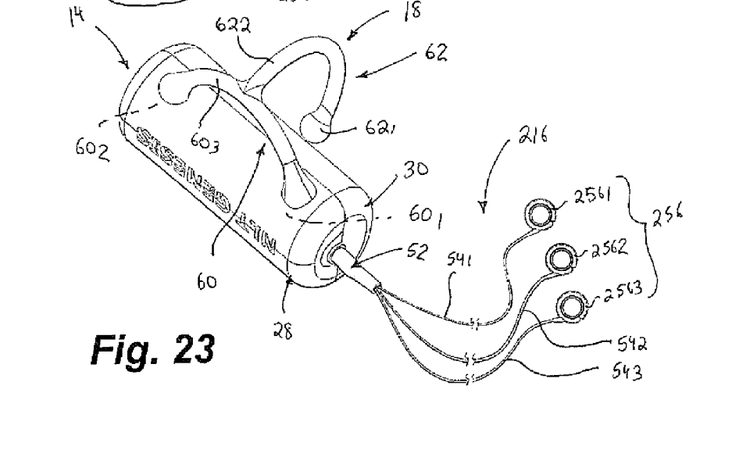
FIG. 23 is a rear-perspective view of the symptom-treatment system of FIG. 22.

A symptom-treatment system 10 in accordance with a first embodiment of the present disclosure is shown in FIGS. 1-3. Another embodiment of a symptom-treatment system 210 is shown in FIGS. 22 and 23. An illustrative method of coupling symptom-treatment system 10 to a patient's ear 12 is shown in FIGS. 16-21 so that therapy may be provided to the patient. An illustrative assembly method used to assemble symptom-treatment system 10 is shown in FIGS. 4-15.

Figures 20, 21:
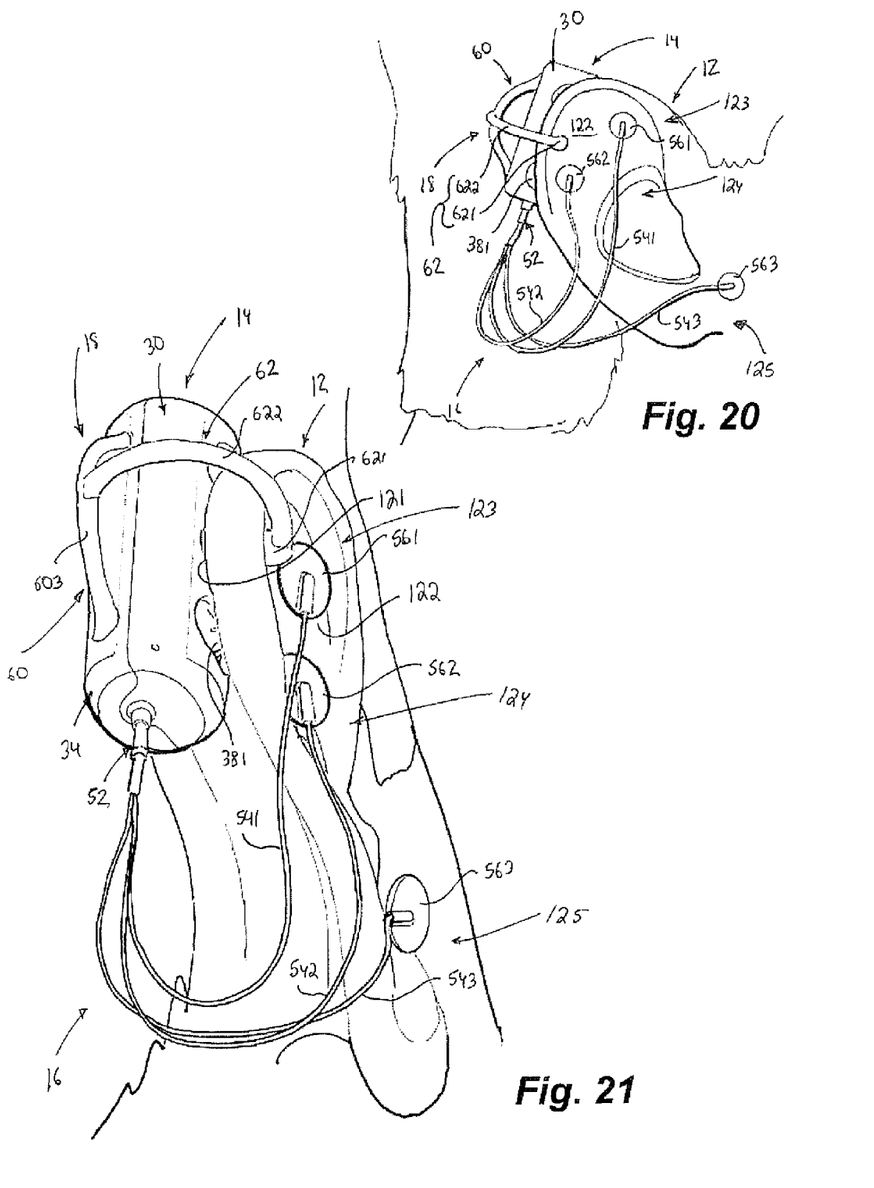
FIG. 20 is a view similar to FIG. 19 showing the control unit coupled to the patient's ear and showing that each of the three treatment applicators has been coupled to three separate locations on the front surface of the patient's ear.
FIG. 21 is a view similar to FIG. 18 showing the treatment applicators coupled to the front surface of the patient's ear.

Pain-management system 10 includes a control unit 14, a treatment unit 16 coupled to control unit 14, and a control-unit mount 18 as shown in FIGS. 1 and 2. Control-unit mount 18 is configured to provide means for coupling selectively control unit 14 to patient's ear 12 at a location on patient's ear 12 where treatment unit 16 is coupled to control unit 14 and to patient's ear 12 so that a therapeutic treatment may be communicated from control unit 14 through treatment unit 16 and into patient's ear 12 as shown in FIGS. 20 and 21.

Control unit 14 includes, for example, a control-unit housing 20, a power unit 22, and a control board 24 as shown in FIG. 3. Control-unit housing 20 is formed to include a component space 26 that is configured to receive power unit 22 and control board 24 therein. Power unit 22 and control board 24 cooperate together to provide means for generating and sending a treatment signal to treatment unit 16. As an example, the treatment signal provides about 4.2 V to the patient's skin and about 3.8 V to an area in or below the skin. The treatment signal may be provided to the patient with a frequency in a range of about 1 Hz to about 100 Hz.

Control-unit housing 20 includes an upper mount shell 28 and a lower control-unit foundation 30 as shown in FIG. 3. Lower control-unit foundation 30 is formed to include a plug aperture 32 that is arranged to open into component space 26. Component space 26 is defined by upper mount shell 28 and lower control-unit foundation 30.

Lower-control unit foundation 30 includes a foundation shell 34 and a grounding plate 36 as shown in FIG. 3. Foundation shell 34 is coupled to grounding plate 36 by a grounding-plate over-mold connection 70. As suggested in FIG. 1 and shown in FIG. 3, grounding plate 36 include a set 38 of three grounding terminals 381, 382, 383. Foundation shell 34 is formed to include set 42 of terminal apertures 421, 422, 423 as shown in FIGS. 1 and 3. Grounding terminals 381, 382, 383 are arranged to extend away from component space 26 toward rear surface 121 of patient's ear 12 and contact rear surface 121 of patient's ear 12 as suggested in FIGS. 16-19.

Figure 9:
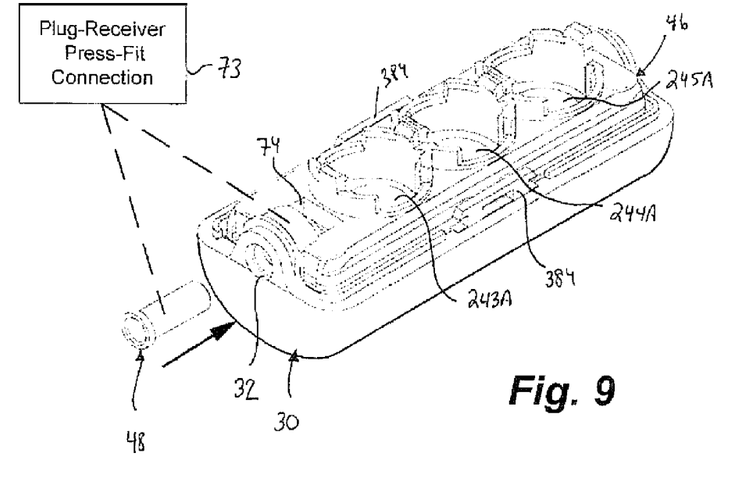
FIG. 9 is an enlarged perspective and diagrammatic view showing a third assembly operation in which the plug receiver is coupled to the control-unit foundation and the power-source carrier by a plug-receiver press-fit connection.
Figure 10:
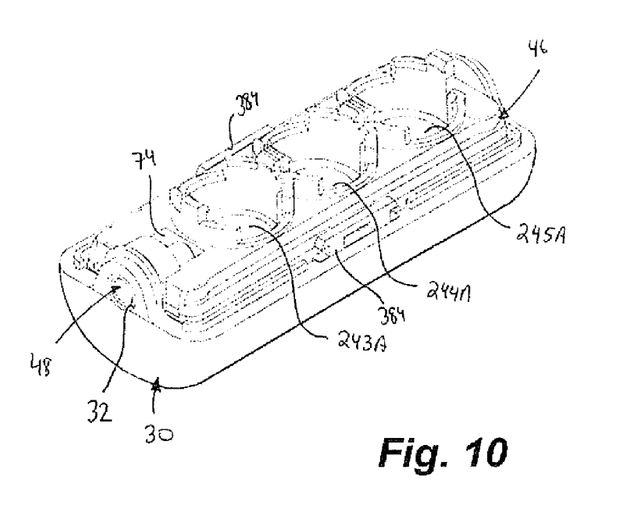
FIG. 10 is a view similar to FIG. 9 showing the plug receiver coupled to the control-unit foundation and the power-source carrier after the third assembly operation has been completed.
Figure 11:
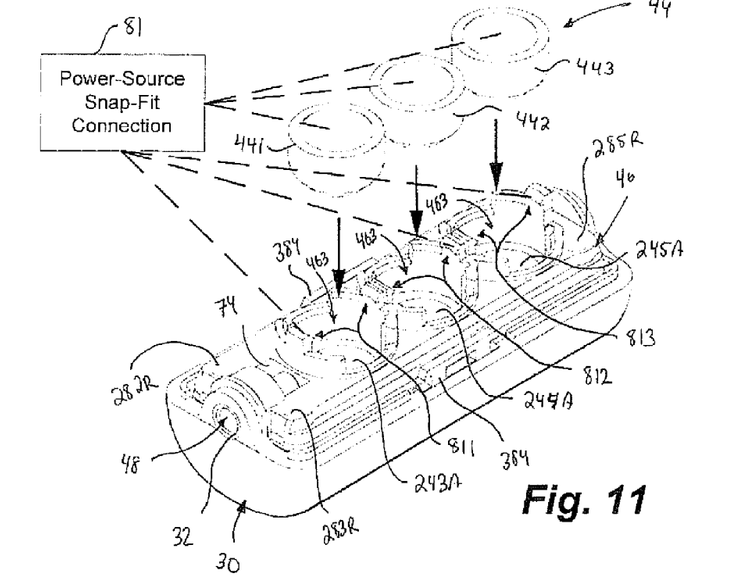
FIG. 11 is an enlarged perspective and diagrammatic view showing a fourth assembly operation in which each battery included in the set of batteries is coupled to an associated battery receiver included in the power-source carrier by a battery snap-fit connection.
Figure 12:
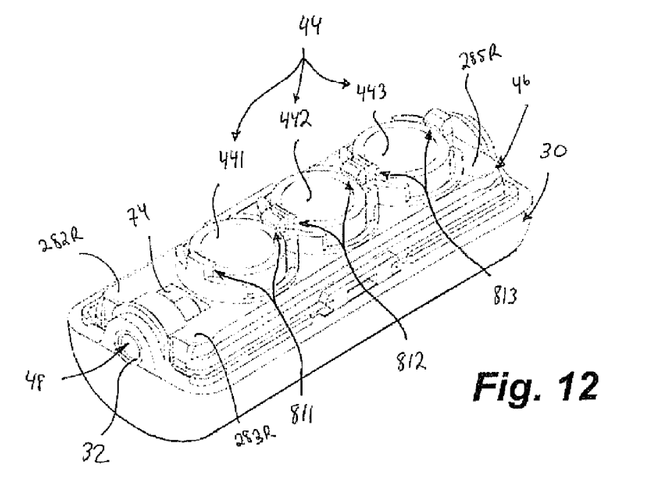
FIG. 12 is a view similar to FIG. 11 showing the set of three batteries coupled to the power-source carrier after the fourth assembly operation has been completed.
Figure 13:
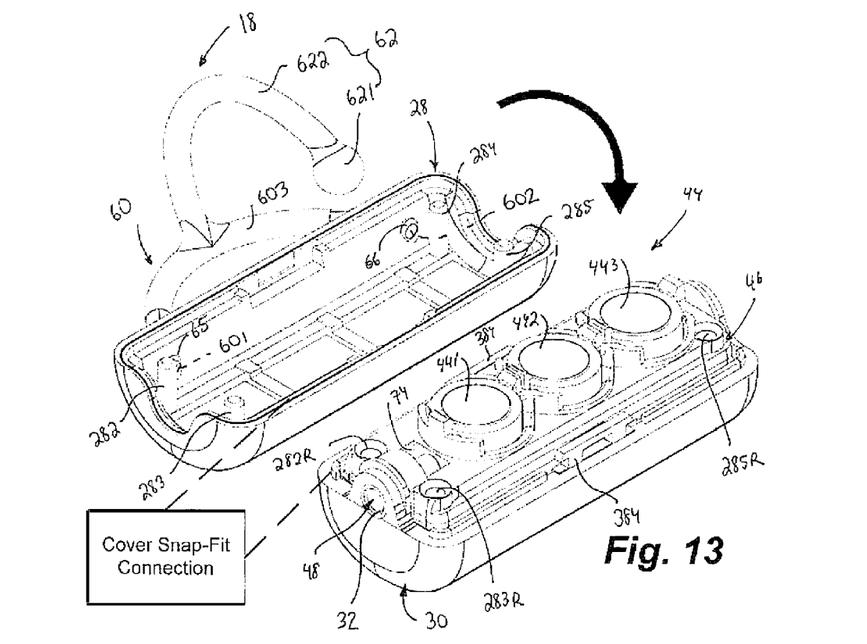
FIG. 13 is an enlarged perspective and diagrammatic view showing a fifth assembly operation in which C-shaped mount and mount shell are coupled to the control-unit foundation by a mount-shell snap-fit connection.

Grounding terminals 381, 382, 383 cooperate with power unit 22 and control board 24 to complete an electrical circuit so that therapy may be provided to the patient as suggested in FIGS. 20 and 21. Power unit 22 includes a power source 44, a power-source carrier 46, and a plug receiver 48 as shown in FIG. 3. Power source 44 includes, for example, three round batteries 441, 442, 443. Power source 44 is carried in power-source carrier 46 and arranged so that each battery 441, 442, 443 is coupled electrically to control board 24 as shown in FIGS. 11 and 12. Plug receiver 48 is arranged to extend through plug aperture 32 to couple to control-unit foundation 30 by a plug-receiver press-fit connection 50 as shown in FIGS. 9 and 10.

Plug receiver 48 is configured to interconnect treatment unit 16 to control unit 14 so that the treatment signal produced by power unit 22 and control board 24 may be transmitted to patient's ear 12. Treatment unit 16 includes, for example, a wire-harness plug 52, a wire harness 54, and a set 56 of treatment applicators 561, 562, 563 as shown in FIGS. 1-3. Wire harness 54 illustratively includes first, second, and third connection wires 541, 542, 543. Each connection wire 541, 542, 543 includes a distal end coupled to associated treatment applicator 561, 562, 563 and an opposite proximal end coupled to wire-harness plug 52. Wire-harness plug 52 is arranged to extend through plug aperture 32 and into plug receiver 48 so that each wire 541, 542, 543 and associated treatment applicator 561, 562, 563 is coupled electrically to control board 24 and power unit 22 to receive the treatment signal.

Figure 15:
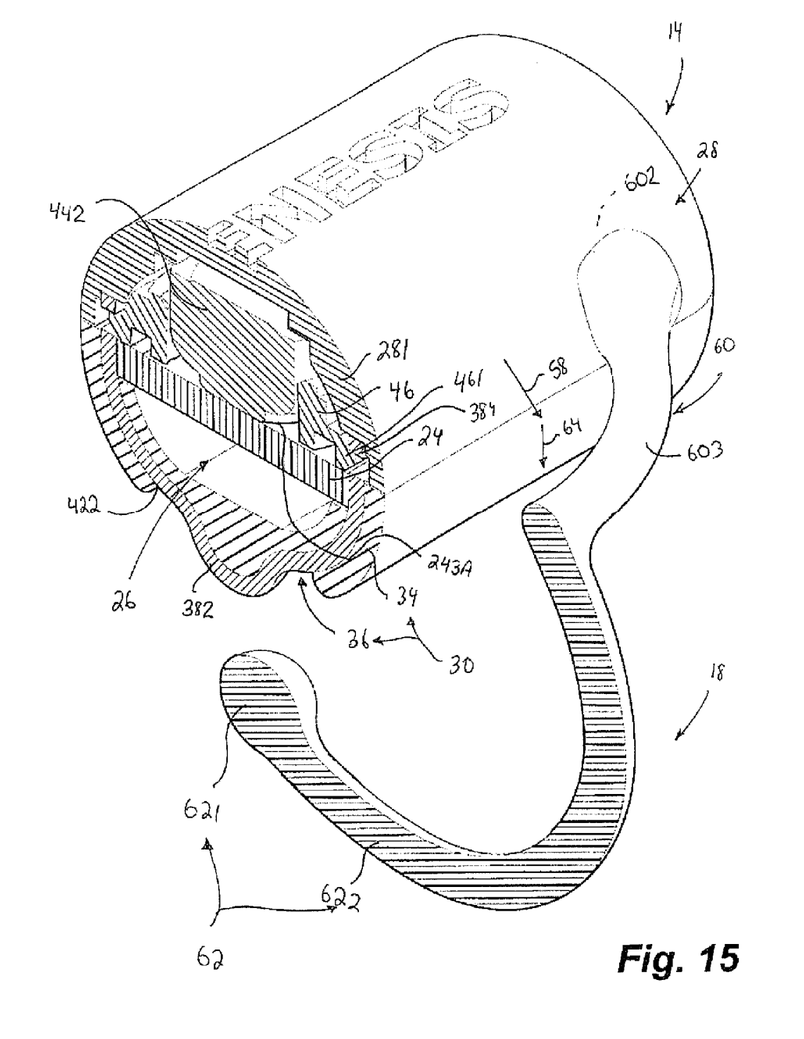
FIG. 15 is a sectional view taken along line 15-15 of FIG. 14.

During application of the treatment signal to patient's ear 12, control unit 12 is mounted on patient's ear 12. Control unit 12 is mounted to patient's ear 12 using control-unit mount 18 which includes a mount bracket 60 and a mount arm 62 as shown in FIGS. 1-3. Mount bracket 60 is coupled to upper mount shell 28 and is arranged to extend away from mount shell 28 in a radial direction 58 as shown in FIG. 2. Mount arm 62 is appended to mount bracket 60 and arranged to extend away from mount bracket 60 in a tangential direction 64 as shown in FIG. 15. Mount arm 62 curves around control unit 14 to cause a retention end 621 of mount arm 62 to be located in spaced-apart relation below second grounding terminal 382. When control unit 14 is mounted on patient's ear 12, grounding terminals 381, 382, 383 engage and touch rear surface 121 of patient's ear 12 and retention end 621 of mount arm 62 engages and mates with a front surface 122 of patient's ear 12 as shown in FIGS. 18-21.

Mount bracket 60 includes a first mount post 601, a second mount post 602, and a band 603 as shown in FIG. 3. First mount post 601 is coupled to one end of band 603 and second mount post 602 is coupled to an opposite end of band 603. Each mount post 601, 602 is arranged to extend into associated post receivers 65, 66 formed in mount shell 28. As an example, mount posts 601, 602 may be coupled to mount shell 28 by a snap-fit connection, glue, or any other suitable alternative.

Mount arm 62 includes retention end 621 that is arranged to engage front surface 122 of patient's ear 12 to cause patient's ear 12 to be trapped between grounding posts 381, 382, 383 and retention end 621 of mount arm 62. Retention end 621 is coupled to mount bracket 60 by an arm strip 622 as shown in FIG. 3. A first end of arm strip 622 is appended to mount bracket 60 while retention end 621 is appended to an opposite second end of arm strip 622.

Figure 4:
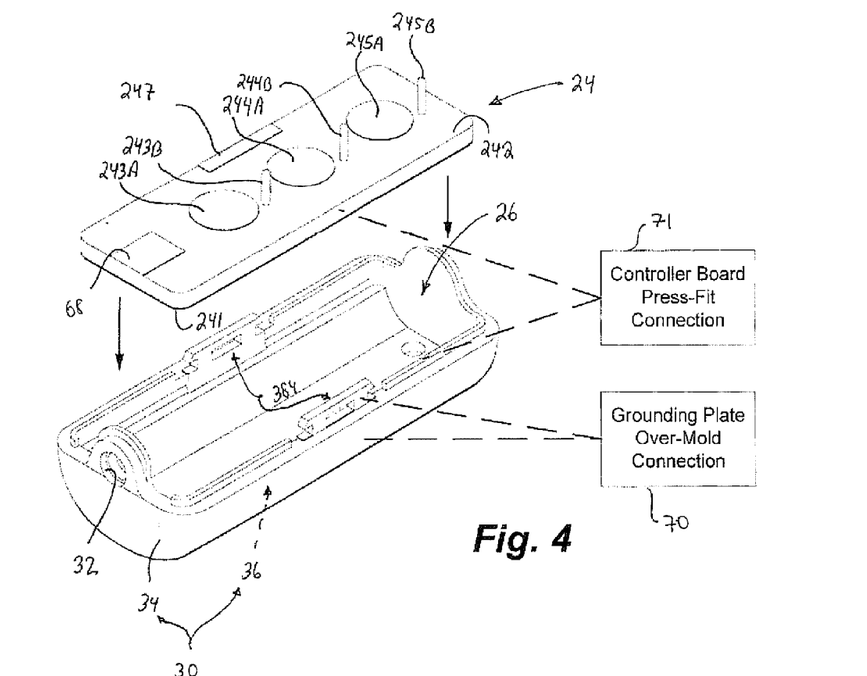
FIG. 4 is an enlarged perspective and diagrammatic view showing a first assembly operation in which the control board is coupled to the control-unit foundation using a controller-board press-fit connection and suggesting that the grounding plate is coupled to the foundation shell by a grounding-plate over-mold connection.
Figure 5:
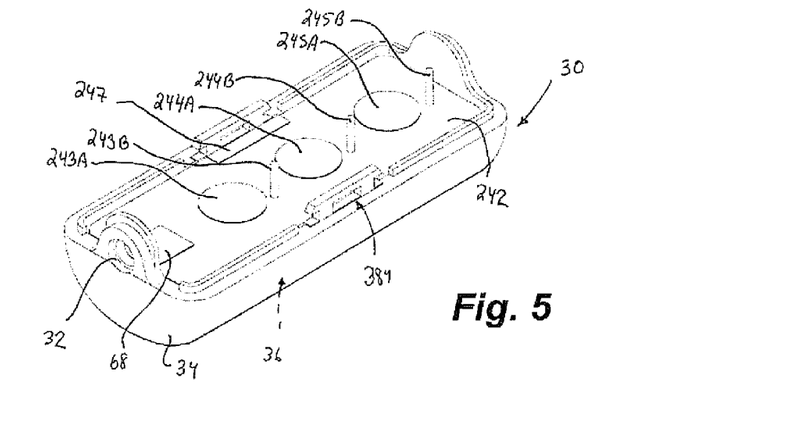
FIG. 5 is a view similar to FIG. 4 showing the control board coupled to the control-unit foundation after the first assembly operation has been completed.

Control unit 14 is assembled in an illustrative assembly process shown in FIGS. 4-15. In a first assembly operation, control board 24 is coupled to the control-unit foundation 30 using a controller-board press-fit connection 71 as shown in FIGS. 4 and 5. Control board 24 includes a first side 241 and an opposite second side 242. First side 241 is arranged to face toward foundation shell 34. Control board 24 further includes a control chip 246 that is coupled to first side 24 and ground interface 247 that is coupled to first side 241 and configured to interconnect control board 24 and grounding plate 36 as shown in FIGS. 4 and 5.

Control chip 246 interconnects power unit 22 and treatment unit 16 to cause the treatment signal to be provided. Second side 242 faces opposite first side 241 and includes first, second, and third power interfaces 243, 244, 245. Each power interface 243, 244, 245 includes a negative terminal 243A and a positive terminal 243B as shown in FIG. 4. Each negative terminal 243A, 244A, 245A is illustratively round pad that is configured to couple electrically to a negative portion of the associated battery. Each positive terminal 243B, 244B, 245B is illustratively an upstanding pin that is configured to couple electrically to a positive portion of the associated battery.

Figure 6:
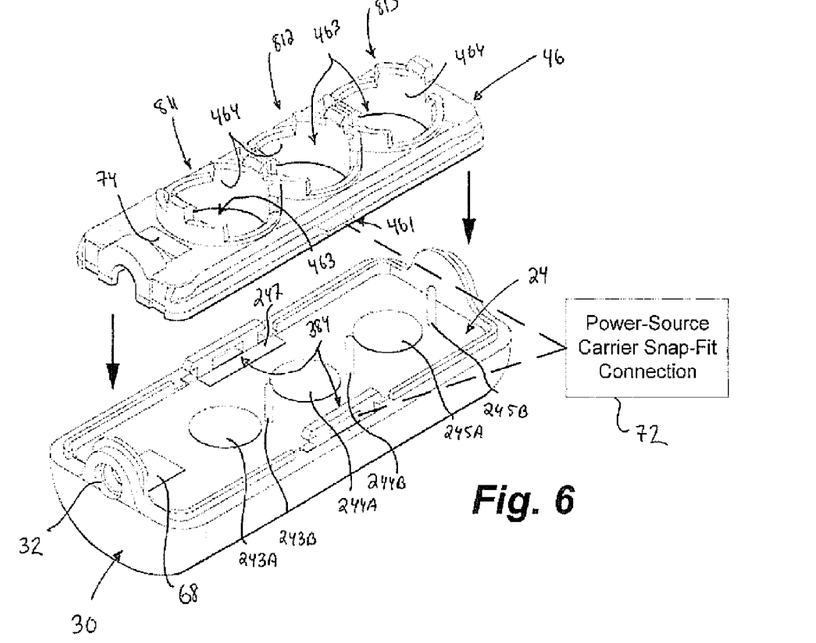
FIG. 6 is an enlarged perspective and diagrammatic view showing a second assembly operation in which the power-source carrier is coupled to the control-unit foundation by a power-source carrier snap-fit connection.
Figure 7:
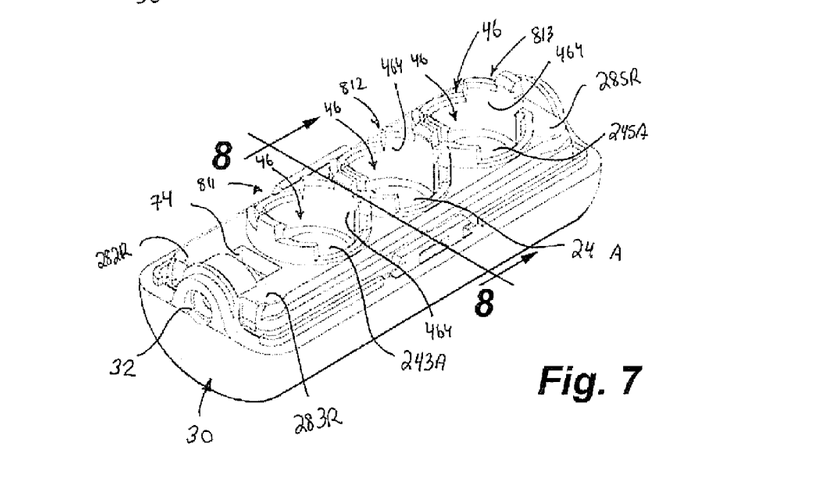
FIG. 7 is a view similar to FIG. 6 showing the power-source carrier coupled to the control-unit foundation after the second assembly operation has been completed.
Figure 8:
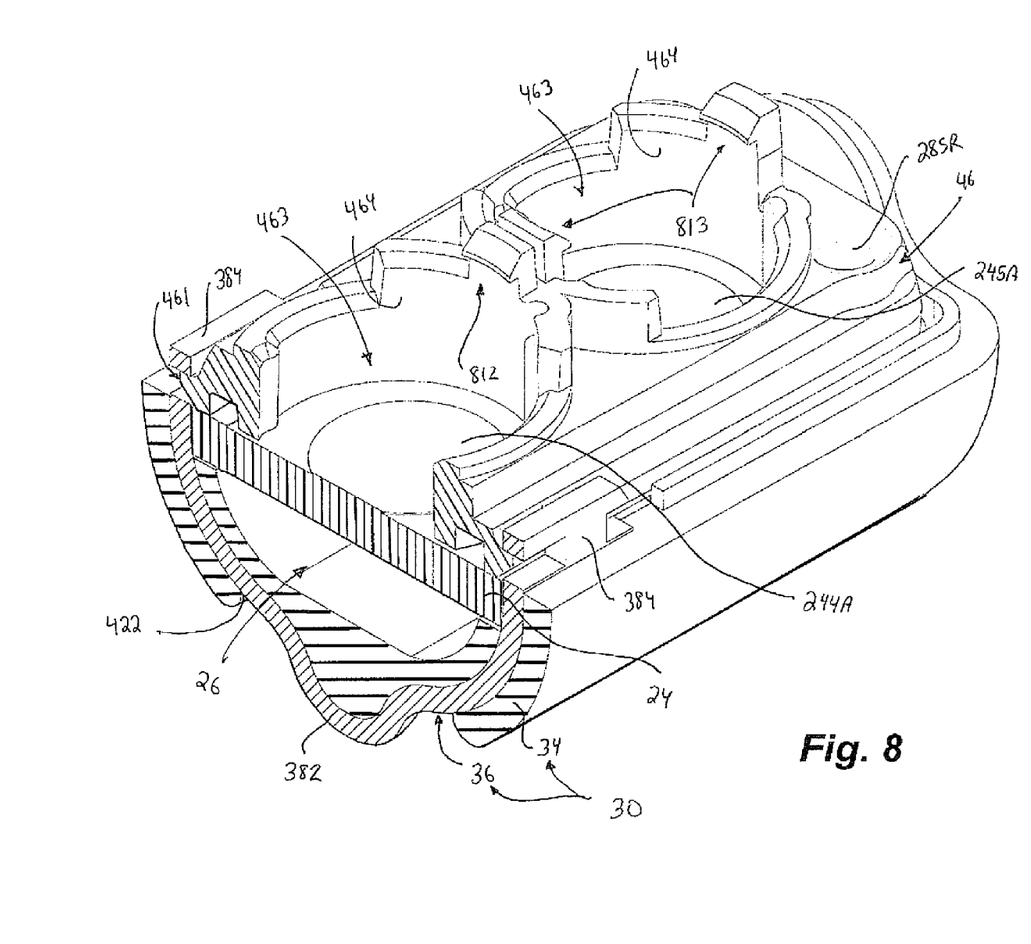
FIG. 8 is a sectional view taken along line 8-8 of FIG. 7 showing a carrier retainer included in the power-source carrier that is mated with a carrier-retainer receiver included in the grounding plate and showing that the foundation shell is over molded around the grounding plate and is formed to include a set of terminal apertures through which the grounding terminals of the grounding plate are arranged to extend to contact the rear surface of the patient's ear.

In a second assembly operation, power-source carrier 46 is coupled to the grounding plate 36 of control-unit foundation 30 using a power-source snap-fit connection 72 as shown in FIGS. 6-8. Power-source snap-fit connection 72 results from mating a carrier retainer 461 included in power-source carrier 46 with a carrier-retainer receiver 384 included in grounding plate 36.

In a third assembly operation, plug receiver 48 is arranged to extend through plug aperture 32 and couple to control-unit foundation 30 by plug-receiver press-fit connection 50 as shown in FIGS. 9 and 10. Plug receiver 48 is also coupled to a signal-output pad 68 included on second side 242 of control board 24. As an example, plug receiver 48 may be coupled to control board 24 by conductive glue, solder, or any other suitable alternative.

In a fourth assembly operation, each battery 441, 442, 443 included in power source 44 is couple to power-source carrier 46 by associated power-source snap-fit connection 81 as shown in FIGS. 11 and 12. Power-source snap-fit connection 81 results from battery retainers 811, 812, 813 being included in power-source carrier 46. Each battery retainer 811, 812, 813 is associated with each battery 441, 442, 443. Power-source carrier 46 is also formed to include a plug-receiver aperture 74 that is arranged to open through power-source carrier 46 and is configured to provide means for applying conductive glue or solder to plug receiver 48.

Each battery retainer 811, 812, 813 is formed to includes a battery-storage space 463, a battery-installation aperture 464 arranged to open into battery-storage space 463, and a battery-contact aperture 465 arranged to open into battery-storage space 463 so that the negative portion of the associated battery is in electrical contact with each associated negative terminal 243A, 244A, 245A. As an example, each battery 441, 442, 443 is pressed downwardly through battery-installation aperture 464 into battery-storage space 463 as shown in FIGS. 11 and 12.

Figure 14:
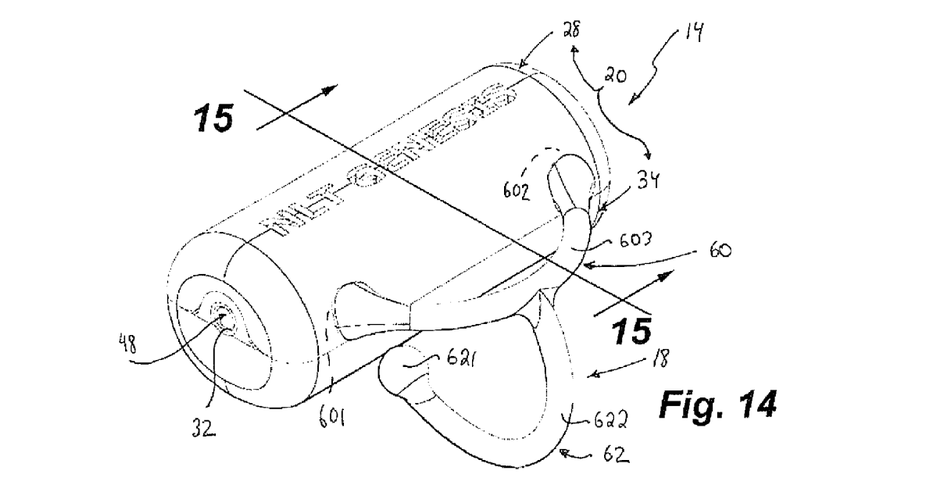
FIG. 14 is a view similar to FIG. 13 showing the mount shell and C-shaped mount coupled to the control-unit foundation after the fifth assembly operation has been completed.

In a fifth assembly operation, upper mount shell 28 and interconnected control-unit mount 18 is coupled to foundation shell 34 by a cover snap-fit connection 73 as shown in FIGS. 12 and 14. Mount shell 28 includes a mount-shell body 281 and four mount-shell posts 282, 283, 284, 285 that are arranged at four corners of the mount shell 28 and arranged to extend away from mount-shell body 281 and into component space 26. As an example, each mount-shell post 282, 283. 284, 285 is arranged to mate with an associated post receiver 282R, 283R, 284R, 285R formed in power-source carrier 46. Mount-shell posts 282, 283, 284, 285 and associated post receivers 282R, 283R, 284R, 285R operate to retainer power-source carrier 46 and power source 44 during assembly and operation of pain-management system 10.

Figure 16:
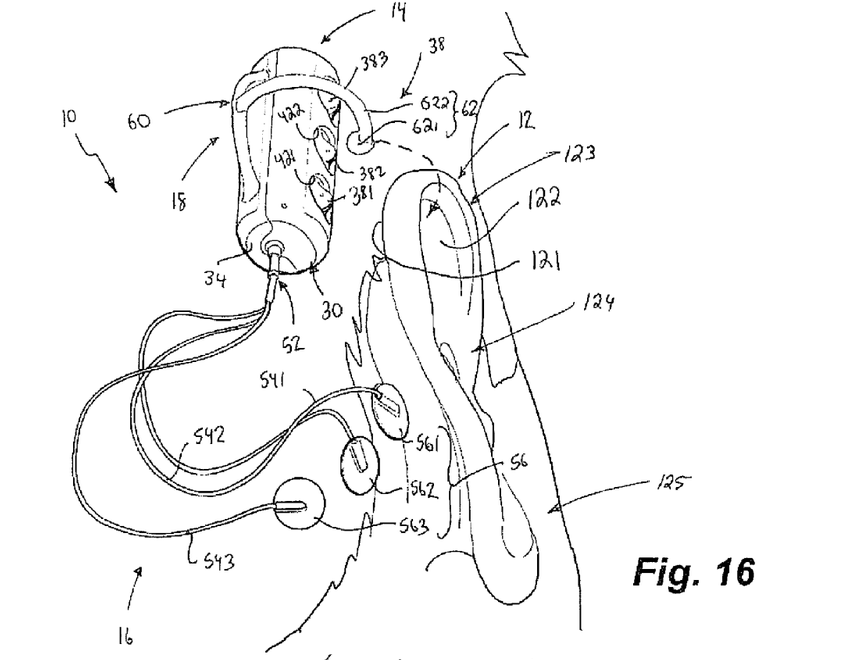
FIG. 16 is a rear perspective view showing the symptom-treatment system of FIGS. 1 and 2 before the control unit is coupled to the patient's ear using the C-shaped mount.
Figure 17:
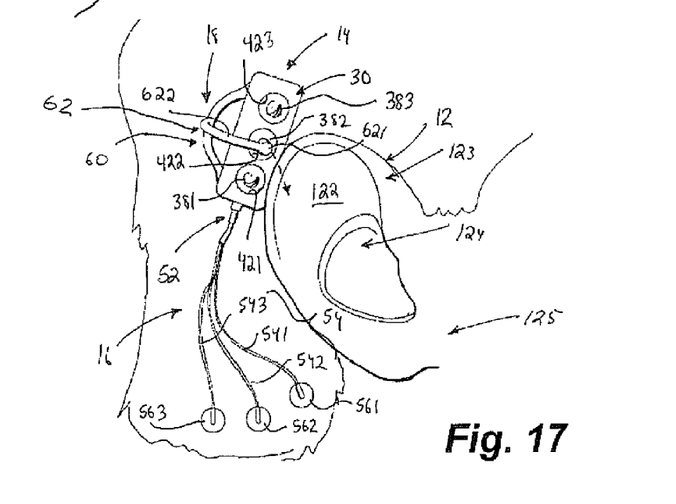
FIG. 17 is a right-side elevation view showing the symptom-treatment system before the control unit is coupled to the patient's ear using the C-shaped mount.

After control unit 14 has been assembled, treatment unit 16 is then coupled to control unit 14 by way of inserting wire-harness plug 52 into plug receiver 48. Pain-management system 10 is then ready for installation on patient's ear 12 as shown in FIGS. 16-21. In a first installation stage, control unit 14 is oriented to cause grounding terminals 381, 382, 383 to engage rear surface 121 of patient's ear 12 and to cause mount arm 62 of control-unit mount 18 to engage front surface 122 of patient's ear as shown in FIGS. 16 and 17.

Figures 18, 19:
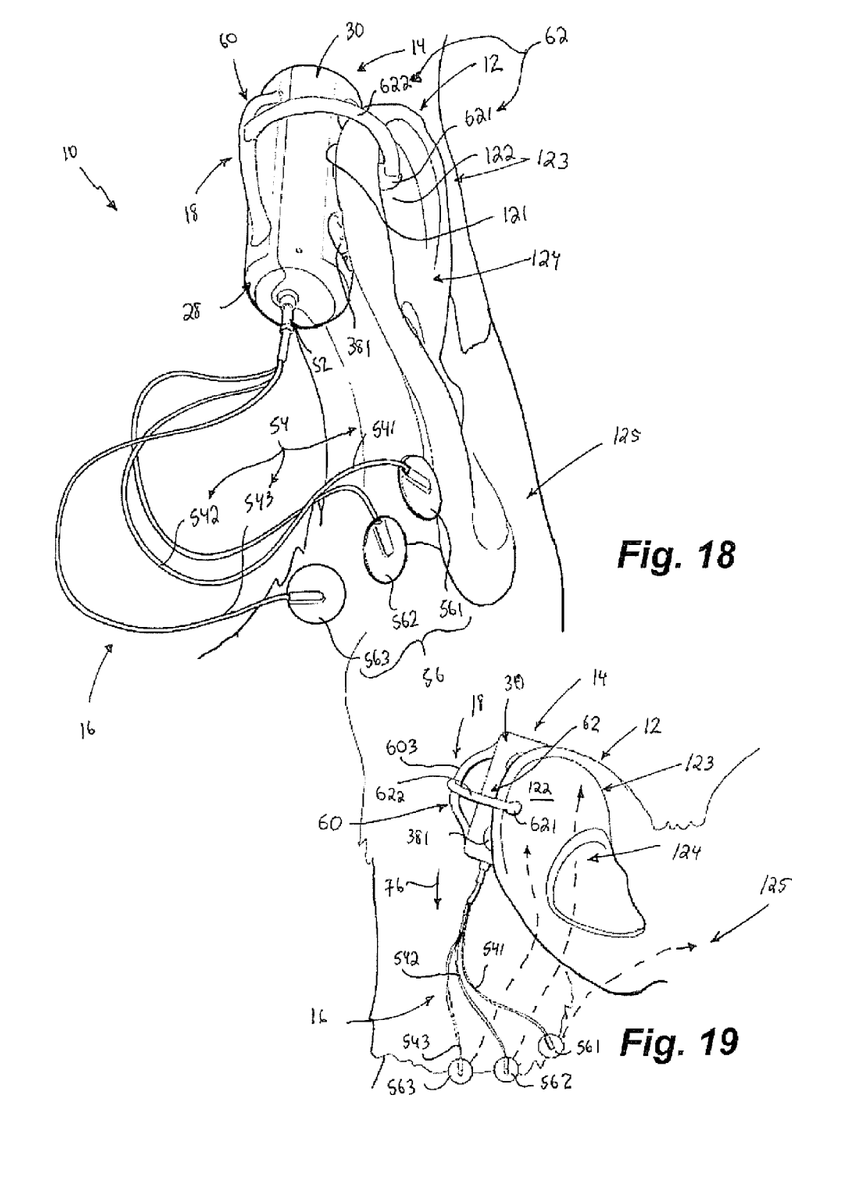
FIG. 18 is a view similar to FIG. 16 showing the control unit coupled to the patient's ear using the C-shaped mount.
FIG. 19 is a view similar to FIG. 17 showing the control unit coupled to the patient's ear using the C-shaped mount and suggesting coupling of the three treatment applicators to the patient's ear as suggested in FIGS. 20 and 21.

In a second installation stage, control unit 14 is positioned on patient's ear 12 to cause patient's ear 12 to be located between retention end 621 of mount arm 62 and grounding terminals 381, 382, 383 included in control unit 14 as shown in FIGS. 18 and 19. At the same time, connection wires 541, 542, 543 and treatment applicators 561, 562, 563 are coupled to control unit 14 by wire-harness plug 52 and left hanging in a downward direction 76 as shown in FIG. 19.

In a third installation stage, treatment unit 16 is coupled to patient's ear 12 as suggested in FIG. 19 and shown in FIGS. 20 and 21. As an example, first treatment applicator 561 is moved to a first location on patient's ear 12 and is coupled to patient's ear 12 at the first location. Second treatment applicator 562 is moved to a second location on patient's ear 12 and is coupled to patient's ear 12 at the second location which is spaced apart from the first location. Third treatment applicator 563 is moved to a third location on patient's ear 12 and is coupled to patient's ear 12 at the third location which is spaced apart from both the first and the second locations. As an illustration, the first location is at a top portion 123 of patient's ear 12, the third treatment location is at a bottom portion 125 of patient's ear, and the third treatment location is at a middle portion 124 of patient's ear 12 which is between top and bottom portions 123, 125.

In one embodiment, treatment applicators 561, 562, 563 are an electrode coupled to the patient's skin so that the treatment signal may pass into the skin and provide therapy to the patient. In another embodiment, treatment applicators include a conductive pad configured to conduct the treatment signal from the associated connection wire to the patient's skin and an adhesive layer. The conductive pad has a diameter of about ⅜ inches and is made from carbide loaded vinyl. The adhesive layer is coupled to a first side of the pad and is configured to couple removably the conductive pad to the patient's skin.

In yet another embodiment, the treatment applicator includes the conductive pad, the adhesive layer, and a needle. The needle is coupled to the conductive pad and arranged to extend toward and into the patient's skin to maximize transmission of the treatment signal into the patient's skin. In still yet another embodiment, treatment applicators include the conductive pad, the adhesive layer, and a metal bead coupled to the conductive pad and arranged to extend toward and engage the patient's skin to maximize transmission of the treatment signal into the patient's skin.

Another embodiment of pain-management system 210 is shown in FIGS. 22 and 23. Pain-management system 210 includes control unit 14, treatment unit 216 coupled to control unit 14, and control-unit mount 18 as shown in FIGS.

1 and 2. Treatment unit 216 includes, for example, wire-harness plug 52, wire harness 54, and a set 256 of treatment applicators 2561, 2562, 2563 as shown in FIGS. 22-23. Treatment applicators 2561, 2562, 2563 are configured to mate with associated needles which were previously implanted on front surface 122 of patient's ear 12. As an example, each treatment applicator 2561, 2562, 2563 is configured to transmit the electrical signal provided by power unit 22 and control board 24 to the needles.

The invention claimed is:

1. A pain management device comprising:
a control unit configured to provide a treatment signal,
a treatment unit comprising a plurality of treatment applicators configured to be located at selected locations on a patient's skin, the treatment unit having a wired connection to the control unit for interconnecting the control unit and the patient's skin to cause the treatment signal to be transmitted to the patient's skin,
a control unit housing containing the control unit and a power source, at least a portion of the control unit housing being electrically conductive and
a control unit mount configured to removably attach the control unit housing to an ear of the patient at a location on the ear where the treatment unit is coupled to the control unit and the ear so that a therapeutic treatment can be provided to the patient in response to communication of the treatment signal from the control unit through the treatment applicators of the treatment unit and the ear:
wherein the control unit mount includes a mount bracket coupled to the control unit and arranged to extend away from the control unit in a radial direction and a mount arm appended to the mount bracket and arranged to extend away from the mount bracket and curve around the control unit.

2. The pain management device of claim 1, wherein the mount bracket and the mount arm are configured to compress against the ear to hold the device to the ear.

3. The pain management device of claim 2, the control unit mount arm being arranged to curve around the control unit to cause a retention end of the mount arm to be located in spaced apart relation to the control unit.

4. The pain management device of claim 1, the control unit housing including a component space therein, the power source arranged to lie in the component space, and a control board arranged to lie in the component space and coupled to the power source to provide the treatment signal.

5. The pain management device of claim 1, the control unit housing including a grounding plate coupled to a control board and arranged to contact the patient's skin to cause an electrical circuit to be formed that includes the power source, the control board, the grounding plate, and the patient.

6. The pain management device of claim 1, the treatment unit comprising a wire harness for interconnecting the control unit and the plurality of treatment applicators.

7. A pain management device comprising:
a control unit configured to provide a treatment signal,
a treatment unit constructed and arranged to be coupled to a patient's skin, the treatment unit having a wired connection to the control unit for interconnecting the control unit and the patient's skin to cause the treatment signal to be transmitted to the patient's skin,
a control unit housing containing the control unit and a power source, at least a portion of the control unit housing being electrically conductive and
a control unit mount comprising a mount bracket coupled to the control unit and a mount arm, wherein said control unit mount is configured to removably attach the control unit housing to an ear of the patient such that the treatment unit is coupled to the control unit and the ear so that a therapeutic treatment can be provided to the patient in response to communication of the treatment signal from the control unit through the treatment unit and the ear;
wherein the mount bracket is arranged to extend away from the control unit in a radial direction and the mount arm is appended to the mount bracket and arranged to extend away from the mount bracket and curve around the control unit; and
wherein said control unit housing is positioned such that said electrically conductive portion of the control unit housing is in contact with a rear surface of the patient's ear.

* * * * *